United States Patent
Jones et al.

(10) Patent No.: US 11,253,458 B2
(45) Date of Patent: Feb. 22, 2022

(54) PERSONAL CARE COMPOSITION COMPRISING PARTICLES

(71) Applicant: Conopco, Inc., Englewood Cliffs, NJ (US)

(72) Inventors: Christopher Clarkson Jones, Wirral (GB); Xiaoyun Pan, Shanghai (CN); Su Yuan, Shanghai (CN); Qiqing Zhang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 48 days.

(21) Appl. No.: 16/343,015

(22) PCT Filed: Sep. 29, 2017

(86) PCT No.: PCT/EP2017/074777
§ 371 (c)(1),
(2) Date: Apr. 18, 2019

(87) PCT Pub. No.: WO2018/077570
PCT Pub. Date: May 3, 2018

(65) Prior Publication Data
US 2020/0054543 A1 Feb. 20, 2020

(30) Foreign Application Priority Data

Oct. 28, 2016 (WO) ................ PCT/CN2016/103834
Dec. 20, 2016 (EP) ..................................... 16205435

(51) Int. Cl.
*A61K 8/73* (2006.01)
*A61K 8/02* (2006.01)
*A61K 8/891* (2006.01)
*A61Q 5/12* (2006.01)

(52) U.S. Cl.
CPC ............ *A61K 8/736* (2013.01); *A61K 8/0241* (2013.01); *A61K 8/891* (2013.01); *A61Q 5/12* (2013.01); *A61K 2800/412* (2013.01); *A61K 2800/624* (2013.01); *A61K 2800/651* (2013.01); *A61K 2800/654* (2013.01); *A61K 2800/94* (2013.01)

(58) Field of Classification Search
CPC ...... A61K 8/736; A61K 8/0241; A61K 8/891; A61K 2800/412; A61K 2800/624; A61K 2800/651; A61K 2800/654; A61K 2800/94; A61K 8/0258; A61Q 5/12
See application file for complete search history.

(56) References Cited

U.S. PATENT DOCUMENTS

| | | | |
|---|---|---|---|
| 6,534,091 B1 | 3/2003 | Garces Garces et al. | |
| 6,733,790 B1 | 5/2004 | Garces Garces | |
| 6,818,296 B1 | 11/2004 | Garces Garces et al. | |
| 6,979,467 B1 | 12/2005 | Garces Garces et al. | |
| 2001/0053803 A1 | 12/2001 | Kuwahara et al. | |
| 2006/0073209 A1 | 4/2006 | Sung et al. | |
| 2007/0181038 A1 | 8/2007 | Sabesan et al. | |
| 2007/0286837 A1 | 12/2007 | Torgerson et al. | |
| 2009/0013481 A1 | 1/2009 | Colaco et al. | |
| 2009/0258042 A1 | 10/2009 | Anastasiou | |
| 2010/0008870 A1 | 1/2010 | Dihora et al. | |
| 2010/0047202 A1 | 2/2010 | Goddinger et al. | |
| 2010/0173003 A1 | 7/2010 | SenGupta et al. | |
| 2010/0261629 A1 | 10/2010 | Smets et al. | |
| 2011/0071064 A1 | 3/2011 | Lei et al. | |
| 2011/0152147 A1 | 6/2011 | Smets et al. | |
| 2012/0237578 A1 | 9/2012 | Lei et al. | |
| 2014/0079686 A1 | 3/2014 | Barman et al. | |
| 2015/0265541 A1* | 9/2015 | Park ..................... | A61K 9/5089 424/489 |
| 2016/0099680 A1 | 4/2016 | Li et al. | |
| 2016/0106636 A1 | 4/2016 | Speaker et al. | |
| 2016/0028944 A1 | 5/2016 | Chawrai et al. | |

FOREIGN PATENT DOCUMENTS

| | | |
|---|---|---|
| DE | 102007031202 | 3/2009 |
| DE | 102007033184 | 7/2009 |
| DE | 102011079664 | 4/2012 |
| EP | 1257353 | 11/2004 |
| EP | 1813257 | 8/2007 |
| EP | 2865423 | 4/2015 |
| KR | 20070079367 | 8/2007 |
| WO | WO09009657 | 8/1990 |
| WO | WO0147625 | 5/2001 |
| WO | WO0162376 | 8/2001 |
| WO | WO2006041613 | 4/2006 |
| WO | WO2007027711 | 3/2007 |
| WO | WO2008148093 | 12/2008 |
| WO | WO2009020314 | 2/2009 |
| WO | WO2011075556 | 6/2011 |
| WO | WO2012065065 | 5/2012 |

(Continued)

OTHER PUBLICATIONS

Search Report and Written Opinion in PCTEP2017074777; dated Jan. 4, 2018.
Search Report & Written Opinion in EP16205435; dated Feb. 14, 2017.
Written Opinion 2 in PCTEP2017075125.
IPRP2 in PCTEP2017075125; Mar. 12, 2019; .; World Intellectual Property Org. (WIPO).
Search Report and Written Opinion in EP16205438; dated Jun. 27, 2017.

(Continued)

*Primary Examiner* — Quanglong N Truong
(74) *Attorney, Agent, or Firm* — Greenberg Traurig, LLP

(57) ABSTRACT

Disclosed is a personal care composition comprising: a) particle comprising chitosan salt at the outer surface of the particle; and b) silicone component selected from dimethicone, aminosilicone or a mixture thereof, wherein the silicone component has a viscosity of at least 5,000 cSt at 25° C.

11 Claims, No Drawings

(56) References Cited

FOREIGN PATENT DOCUMENTS

| WO | WO2012177986 | 12/2012 |
|----|--------------|---------|
| WO | WO2014064121 | 5/2014 |
| WO | WO2015023961 | 2/2015 |
| WO | WO2015051054 | 4/2015 |
| WO | WO2016000912 | 1/2016 |
| WO | WO2016049456 | 3/2016 |
| WO | WO2016180769 | 2/2017 |

OTHER PUBLICATIONS

Search Report and Written Opinion in PCTEP2017075125; dated Dec. 21, 2017.
Aminosilicone demithicone hair; Google Scolar search; Dec. 19, 2020; pp. 1-2.

\* cited by examiner

PERSONAL CARE COMPOSITION COMPRISING PARTICLES

FIELD OF THE INVENTION

The present invention is related to a person care composition containing particles. In particular, the present invention is related to a person care composition comprising (a) particle comprising chitosan salt at the outer surface of the particle, and (b) silicone component.

BACKGROUND OF THE INVENTION

Many personal care products seek to deliver benefit agents to substrates such as hair, and/or skin. To achieve a long-lasting benefit agent release performance, encapsulation of the benefit agent in particles has been proposed as a means, in particular for the perfume. When applied, the microcapsule may be deposited onto the substrates, for example onto hair, and broken by action of pressure and/or rubbing when consumers wash their hair. The perfume is then released and brings superior sensory to the consumers.

The delivery of the particles is very important for the delivery of the encapsulated benefit agents. However, when the particles are incorporated into a personal care composition, the performance of the composition per se may be compromised due to the existence of particles. For example, the silicone deposition efficiency may be affected in a hair care composition.

Thus, we have recognized a need to develop a personal care composition which the performance of the composition per se was not compromised. Therefore we developed a person care composition comprising particle comprising chitosan salt at the outer surface of the particle. It was found that when including the particles of the present invention and certain silicone of the present invention into the personal care composition, the deposition of silicone onto hair was unexpectedly enhanced.

SUMMARY OF THE INVENTION

In a first aspect, the present invention is directed to a personal care composition comprising: a) particle comprising chitosan salt at the outer surface of the particle; and b) silicone component selected from dimethicone, aminosilicone or a mixture thereof, wherein the silicone component has a viscosity of at least 5,000 cSt at 25° C.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Water insoluble" as used herein refers to that the solubility in water is less than 1 gram per 100 gram of water, preferably less than 1 gram per 1 kilogram of water, at 25° C. and at atmospheric pressure.

Viscosity for the purposes of the present invention means kinematic viscosity at 25° C. and is reported as centiStokes (1 cSt=1 $mm^2 \cdot s^{-1}$) unless otherwise explicitly stated. Viscosity of fluids such as silicone is determined by the relevant international standard, ISO 3104.

One benefit of small particles is that they are less visible in clear products. However, if the particles are too small then it can become difficult to break thereby releasing the benefit agent. Therefore, the particle preferably has an average particle diameter of 0.1 to 50 μm, more preferably from 0.3 to 40 μm, even more preferably from 0.5 to 20 μm, still even more preferably from 1 to 10 μm and most preferably from 1.4 to 6 μm. Diameter of particle means the apparent volume median diameter (D50, also known as ×50 or sometimes d(0.5)) of the particles unless otherwise stated. The diameter may be measurable for example, by laser diffraction using a system (such as a Mastersizer™ 2000 available from Malvern Instruments Ltd).

To have a better deposition on hair, the zeta potential of the particles as measured using a Malvern Nano ZS90 apparatus, in DI water at a solid content of 50 ppm and pH of 7 at 25° C., is preferably at least 5 mV, more preferably at least 15 mV, even more preferably at least 20 mV.

The chitosan salt suitable for the present invention comprises a chitosan component and an anion. Preferably the anion is an organic anion and more preferably an organic anion having a molecular weight of greater than 60, more preferably from 80 to 2000, even more preferably from 80 to 500. Preferably, the chitosan salt is a chitosan-amino acid salt. Preferably the amino acid comprises glutamine, glutamic acid, histidine, leucine, lysine, serine, threonine, arginine or a mixture thereof, more preferably comprises arginine. Most preferably, the chitosan salt is chitosan-arginine salt.

Preferably the chitosan component of the salt (as a protonated material) has a viscosity average molecular weight of at least 10,000 Daltons, more preferably in the range of from 30,000 to 1,000,000 Daltons, even more preferably from 70,000 to 600,000 Daltons, and still even more preferably from 150,000 to 400,000 Daltons. Preferably, the deacetylation degree of the chitosan component is at least 65%, more preferably from 70 to 95%, even more preferably from 72 to 90% and most preferably from 75 to 85%.

Preferably, the chitosan component comprises at least 5%, more preferably at least 10% of protonated primary amino group, by mole of the total amount of primary amino group and protonated primary amino group.

Preferably, the chitosan salt is bound to the particle by means of a covalent bond, entanglement or strong adsorption, more preferably by a covalent bond or entanglement, and most preferably by means of a covalent bond. It is important that the chitosan salt is not removed by water from the particle as it cannot then function effectively as a delivery aid. Thus, for example spray-drier coating of chitosan onto particles would not result in chitosan being an effective delivery aid as the chitosan would be removed from the particles on exposure to water. "Entanglement" as used herein refers to that the chitosan salt is adsorbed onto the particle as the polymerization proceeds and the particle grows in size. It is believed that under such circumstances part of the adsorbed chitosan salt becomes buried within the interior of the particle. Hence at the end of the polymerization, part of the chitosan salt is entrapped and bound in the polymer matrix of the particle, whilst the remainder is free to extend into the aqueous phase.

Typically, the particles comprise benefit agent inside of an inner shell, and an outer shell comprising the chitosan salt at the outer surface of the particle. For sake of clarity, it should be noted that the outer shell is different from the inner shell. Preferably at least 20% of the outer shell by weight, more preferably at least 50% of the outer shell by weight, even more preferably at least 80% by weight of the outer shell is chitosan salt. Most preferably, the outer shell is the chitosan salt.

Various benefit agents can be incorporated into the particles. The benefit agents may include fragrance, pro-fragrance, hair conditioning agent, anti-dandruff agent, moisturizers, emollients, dyes and/or pigments, colour care additives (including dye fixing agents), or a mixture thereof. Preferably, the benefit agent comprises fragrance, pro-fragrance, hair conditioning agent or a mixture thereof. More preferably, the benefit agent is fragrance and/or pro-fragrance, and most preferably the benefit agent is fragrance.

Useful components of the fragrance include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Fragrance and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally fragranced or flavoured, or of modifying the odour and/or taste of said consumer product.

By fragrance in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well-known top-notes include citrus oils, linalool, linalyl acetate, lavender, dihydromyrcenol, rose oxide and cis-3-hexanol. Top notes typically comprise 15-25% wt of a fragrance composition and in those embodiments of the invention which contain an increased level of top-notes it is envisaged at that least 20% wt would be present within the particle.

Another group of fragrances with which the present invention can be applied are the so-called 'aromatherapy' materials. These include many components also used in fragrancery, including components of essential oils such as Clary Sage, *Eucalyptus*, Geranium, Lavender, Mace Extract, Neroli, Nutmeg, Spearmint, Sweet Violet Leaf and Valerian.

Typical fragrance components which it is advantageous to employ in the embodiments of the present invention include those with a relatively low boiling point, preferably those with a boiling point of less than 300, preferably 100-250 Celsius, measured at one atmosphere.

It is also advantageous to encapsulate fragrance components which have a low Log P (i.e. those which will be partitioned into water), preferably with a Log P of less than 3.0.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols.

The fragrance is typically present in an amount of from 10-85% by total weight of the particle, preferably from 15 to 75% by total weight of the particle. The fragrance suitably has a molecular weight of from 50 to 500 Dalton. Pro-fragrances can be of higher molecular weight, being typically 1-10 k Dalton.

Typically the inner shell comprises water insoluble non-polysaccharide polymer, water insoluble inorganic salt or a mixture thereof, more preferably the inner shell comprises water insoluble non-polysaccharide polymer. Inorganic salt may be selected from clay, zeolite, silica, amorphous silicate, crystalline nonlayer silicate, layer silicate, calcium carbonate, sodium carbonate, sodalite, and alkali metal phosphates.

Preferably, the water insoluble non-polysaccharide polymer comprises polyvinyl pyrrolidone, polyvinyl alcohol, cellulose ether, polystyrene, polyacrylate, polymethacrylate, polyolefin, aminoplast polymer, polyacrylamide, acrylate-acrylamide copolymer, melamine-formaldehyde condensate, urea-formaldehyde condensate, polyurethane, polysiloxane, polyurea, polyamide, polyimide, polyanhydride, polyolefin, polysulfone, polysaccaharide, polylactide, polyglycolide, polyorthoester, polyphosphazene, silicone, lipid, polyester, ethylene maleic anyhydride copolymer, styrene maleic anyhydride copolymer, ethylene vinyl acetate copolymer, lactide glycolide copolymer, or combinations of these materials. More preferably, the inner shell comprises polystyrene, polyvinyl alcohol, polyacrylate, polymethacrylates, polyolefins, aminoplast polymer, polyacrylamide, acrylate-acrylamide copolymer, melamine-formaldehyde condensate, urea-formaldehyde condensate, polyurethane, polysaccharide or a mixture thereof. More preferably, the water insoluble non-polysaccharide polymer comprises polystyrene, modified polyvinyl alcohol, polyacrylate, polymethacrylate, polyolefin, aminoplast polymers, melamine-formaldehyde condensate, urea-formaldehyde condensate, polyurethane or a mixture thereof. Even more preferably the water insoluble non-polysaccharide polymer comprises polystyrene, modified polyvinyl alcohol, polyolefin, polyurethane or a mixture thereof. Still even more preferably, the water insoluble non-polysaccharide polymer comprises polystyrene, modified polyvinyl alcohol or a combination thereof and most preferably, the water insoluble non-polysaccharide polymer is polystyrene, modified polyvinyl alcohol, or a combination thereof.

The particle is typically present in the composition at levels of from 0.001% to 10%, preferably from 0.005% to 7.55%, most preferably from 0.01% to 5% by weight of the total composition.

Typically, the silicone component is present in the composition in amount from 0.01 to 10% by weight of the composition, more preferably from 0.1 to 5% by weight of the composition, even more preferably from 0.3 to 4%, still even more preferably from 0.5 to 3% and most preferably from 0.7 to 2.5% by weight of the composition.

The weight ratio of the particle to silicone component is preferably from 1:20 to 5:1, more preferably from 1:10 to 3:1, even more preferably from 1:4 to 1:1.

Preferably, the silicone component is non-volatile. Non-volatile as used herein means having vapour pressure from 0 to 0.1 mm Hg (13.3 Pa), preferably from 0 to 0.05 mm Hg, more preferably from 0 to 0.01 mm Hg at 25° C.

The viscosity of the silicone itself (not the emulsion or the final shampoo composition or mixture of two silicones) is typically from 5,000 to 10,000,000 cSt (centi-Stokes) at 25° C., more preferably from 5,000 to 2,000,000 cSt, even more preferably from 10,000 to 1,500,000 cSt, even more preferably from 300,000 to 1,200,000 cSt.

Preferably the silicone component is emulsified with emulsifier. Suitable emulsifiers for use in the preparation of the aqueous emulsion are well known in the art and includes anionic emulsifier, cationic emulsifier, nonionic emulsifier or mixtures thereof. More preferably, the silicone component is emulsified with non-cationic emulsifier. Even more preferably, the silicone component is emulsified with anionic emulsifier, nonionic emulsifier or a mixture thereof and most preferably with nonionic emulsifier.

Examples of nonionic surfactants suitable for use as emulsifiers for the dimethicone droplets are alkylphenol ethoxylates, e.g., nonylphenol ethoxylate nEO, where n is from 1 to 50 and alcohol ethoxylates, e.g., lauryl alcohol nEO, where n is from 1 to 50, ester ethoxylates, e.g., polyoxyethylene monostearate where the number of oxyethylene units is from 1 to 30.

Preferably the dimethicone suitable for use in the compositions of the invention has a Sauter mean droplet diameter ($D_{3,2}$) of 0.1 to 40 microns, more preferably from 0.2 to 25 microns, even more preferably from 0.5 to 15 microns, still even more preferably from 1 to 12 microns and most preferably from 1.2 to 4 microns. Silicone Sauter mean droplet diameter ($D_{3,2}$) may be measured by laser light scattering using an instrument such as a Malvern Mastersizer.

Preferably, the dimethicone has a viscosity of from 10,000 to 10,000,000 cSt, more preferably from 50,000 to 4,000,000 cSt, even more preferably from 100,000 to 2,000,000 cSt and still even more preferably from 300,000 to 1,200,000 cSt at 25° C. and most preferably from 400,000 to 800,000 cSt.

Aminosilicone means a silicone containing at least one primary, secondary or tertiary amine group, or a quaternary ammonium group. The primary, secondary, tertiary and/or quaternary amine groups may either form part of the main polymer chain or more preferably be carried by a side or pendant group carried by the polymeric backbone. Suitable aminosilicone for use with the invention are described for example in U.S. Pat. No. 4,185,087.

Aminosilicones suitable for use in the invention will typically have a mole % amine functionality in the range of from 0.1 to 8.0 mole %, preferably from 0.1 to 5.0 mole %, most preferably from 0.1 to 2.0 mole %. In general, the amine concentration should not exceed 8.0 mole %.

In a preferred embodiment, the aminosilicone is amodimethicone. Preferably, the amodimethicone has the general formula:

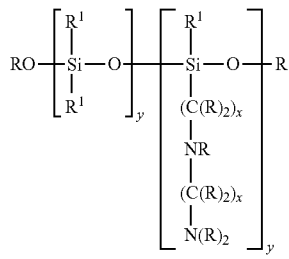

where each R is independently H, or a $C_{1-4}$ alkyl, preferably H; each $R^1$ is independently OR or a $C_{1-4}$ alkyl; and each x is independently an integer from 1 to 4 and each y is greater than zero and independently an integer to yield a polymer having a weigh average molecular weight from 500 to 1 million, and preferably from 750 to 100,000.

The emulsified aminosilicone suitable for use in the compositions of the invention preferably has a Sauter mean droplet diameter in the composition of from 10 nm to 20 microns, preferably from 30 nm to 5 microns, more preferably no greater than 1 micron, even more preferably from 20 nm 600 nm, and most preferably from 20 to 100 nm.

The viscosity of the aminosilicone itself is typically from 5,000 to 500,000 cSt (centi-Stokes) at 25° C., 5,000 to 50,000 cSt, and even more preferably from 10,000 to 30,000 cSt.

Depending on the end-use compositions according to the present invention will typically contain one or more of cationic surfactants, fatty alcohols, anti-dandruff agents, and cationic deposition polymers.

It is preferred that the composition comprises a cationic surfactant. Preferably the cationic surfactant is a quaternary ammonium salt. More preferably, the cationic surfactants have the formula $N+R^1R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. Alkyl groups may be straight chain or branched and, for alkyl groups having 3 or more carbon atoms, cyclic. The alkyl groups may be saturated or may contain one or more carbon-carbon double bonds (eg, oleyl). Preferably, the alkyl groups comprise one or more ester (—OCO— or —COO—) and/or ether (—O—) linkages within the alkyl chain. More preferably, the alkyl groups comprise one or more ether linkages within the alkyl chain. Even more preferably, the cationic surfactant is cetyltrimethylammonium chloride, behenyltrimethylammonium chloride or a mixture thereof. The most preferred cationic surfactant is behenyltrimethylammonium chloride.

Another example of a class of suitable conditioning surfactants for use in the invention, either alone or together with one or more other cationic surfactants, is a combination of (i) and (ii) below:

(i) an amidoamine corresponding to the general formula (I):

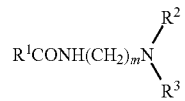

in which R¹ is a hydrocarbyl chain having 10 or more carbon atoms, R² and R³ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which R¹ is a hydrocarbyl residue having from about 11 to about 24 carbon atoms, R² and R³ are each independently hydrocarbyl residues, preferably alkyl groups, having from 1 to about 4 carbon atoms, and m is an integer from 1 to about 4.

Preferably, R² and R³ are methyl or ethyl groups. Preferably, m is 2 or 3, i.e. an ethylene or propylene group.

Particularly preferred amidoamines useful herein are stearamidopropyldimethylamine, stearamidoethyldiethylamine, and mixtures thereof.

A protonating acid may be present. Acid may be any organic or mineral acid which is capable of protonating the amidoamine in the composition. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant. Suitably, the acid is included in a sufficient amount to protonate more than 95 mole % (293 K) of the amidoamine present.

In compositions of the invention, the level of cationic surfactant will generally range from 0.01% to 10%, more preferably 0.05% to 7.5%, most preferably 0.1% to 5% by weight of the composition.

The composition preferably also incorporates a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1% to 8%, more preferably from 0.2% to 7%, most preferably from 0.3% to 6% by weight of the composition.

The weight ratio of cationic surfactant to fatty alcohol is suitably from 1:1 to 1:10, more preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

It is preferred that the composition comprises a cationic deposition polymer, which may assist in deposition of ingredients in the composition. Preferably, the cationic deposition polymer is (or comprises) cationic polygalactomannan, especially guar or *cassia* derived polygalactomannan modified with hydroxypropyl trimonium chloride.

It is highly preferred that compositions according to the invention should contain from 0.01% to 2% wt. of the composition cationic deposition polymer, more preferably from 0.05 to 0.5% wt. and most preferably from 0.08 to 0.25% by weight of the composition.

The composition may additionally comprising antidandruff agent. Suitable antidandruff agents include compounds selected from azole based antifungal agents, octopirox, selenium sulfide, metal pyrithione salts, and mixtures thereof. The preferred azole based antifungal agents are ketoconazole and climbazole. Preferred metal pyrithione salts are zinc, copper, silver and zirconium pyrithione. The most preferred is zinc pyrithione.

Preferably, the antidandruff agent is present at from 0.01 to 5% wt. of the composition, more preferably from 0.1 to 2.5% wt. of the composition.

The composition of the invention may contain other ingredients for enhancing performance and/or consumer acceptability. Such ingredients include dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

The composition preferably comprises at least 30% of water by weight of the composition, more preferably from 35 to 99%, even more preferably from 45 to 95%, still even more preferably from 55 to 92%, most preferably from 65 to 90% by weight of the total composition.

Preferably the personal care composition is a hair treatment composition and more preferably a hair conditioner.

The invention will now be described with reference to the following non-limiting examples.

EXAMPLES

Materials

| Material | Supplier | Description |
| --- | --- | --- |
| Melamine Formaldehyde (MF) fluorescent capsules latex | Givaudan (Mechacaps perfecta P7) | particle diameter of 20 μm, particle solids content is 45.3%, 40% perfume loading in the slurry |
| Chitosan | Aldrich | cat. # 448877, deacetylation degree: 75-85% |
| Ethanol | Sinopharm Chemical | AR grade |
| Acetic Acid | Sinopharm Chemical | AR grade |
| Formic acid | Sinopharm Chemical | AR grade |
| Sodium chloride | Sinopharm Chemical | AR grade |

Example 1

This example demonstrates the preparation of particle.

1a) Preparation of Chitosan Complex 2.5 g of chitosan was added to 500 ml of 0.25% aqueous acetic acid solution and the mixture was agitated until chitosan dissolved completely, this yields a 0.5% Chitosan-Ac solution. Then 675 mg of arginine was added into the chitosan solution and the mixture was stirred overnight. The resultant aqueous product was denoted as Chitosan-Arg complex.

1b) Mixing of MF Slurry with Chitosan Complex 245 g of Chitosan-Arg complex solution was put into a beaker and homogenized. 70 g of diluted MF particles slurry (5 wt % of MF particle) was added dropwise to the Chitosan-Arg complex solution under homogenization. Then, the mixture was transferred to a flask and stirred at 75° C. The dosing ratio of chitosan complex to MF capsule was 1:3 (weight).

1c) Grafting of Chitosan Complex into MF Capsules 4.85 g of formaldehyde (37% aqueous solution) was diluted by 11 g of DI water in a flask. 2.5 g of melamine and 0.1 g of sodium chloride were then added. The pH of the mixture was adjusted to 8.9 by sodium carbonate solution. The mixture was stirred at room temperature for 10 minutes and then heated to 62° C. until it turned into a clear solution (melamine-formaldehyde prepolymer solution with prepolymer solids of 23.2 wt %).

After the temperature of the mixture prepared in section 1b) was raised to 75° C., 0.8 g of melamine-formaldehyde prepolymer solution was added and the pH of the final mixture was adjusted to 3.9 using aqueous formic acid solution. The mixture was then stirred at 75° C. under 400 rpm for about two hours and then cooled to room temperature.

The resultant slurry was washed to remove the un-grafted Chitosan-Arg complex. The final concentrated slurry was denoted as MF-graft-Chitosan-Arg with particle solids content of around 13 wt %.

1d) Characterization of Chitosan Complex Modified MF Capsule

The zeta potentials of MF-graft-Chitosan-Arg and MF particle were measured by zeta potential analyzer (Zetasizer Nano ZS90, Malvern, USA) at 25° C. The particles were dispersed in water with solid content of 50 ppm and the pH of the dispersion was adjusted to about 7 for measurement. Each test was repeated three times. The zeta potential was 71 mV and −60 mV for MF-graft-Chitosan-Arg and MF particle respectively.

Example 2

This example demonstrates the preparation of hair conditioner.

TABLE 1

| Ingredient | Samples (active wt %) | | | | | | | |
|---|---|---|---|---|---|---|---|---|
|  | A | B | C | D | E | 1 | F | 2 |
| Cetearyl alcohol | 4.000 | 4.000 | 4.000 | 4.000 | 4.000 | 4.000 | 4.000 | 4.000 |
| Stearamidopropyl dimethylamine | 1.000 | 1.000 | 1.000 | 1.000 | 1.000 | 1.000 | 1.000 | 1.000 |
| Behenyltrimethyl ammonium chloride | 0.700 | 0.700 | 0.700 | 0.700 | 0.700 | 0.700 | 0.700 | 0.700 |
| Lactic acid | 0.286 | 0.286 | 0.286 | 0.286 | 0.286 | 0.286 | 0.286 | 0.286 |
| Potassium chloride | 0.100 | 0.100 | 0.100 | 0.100 | 0.100 | 0.100 | 0.100 | 0.100 |
| Disodium EDTA | 0.100 | 0.100 | 0.100 | 0.100 | 0.100 | 0.100 | 0.100 | 0.100 |
| DC193 [a] | 1.225 | 1.225 | — | — | — | — | — | — |
| DC949 [b] | — | — | 1.225 | 1.225 | — | — | — | — |
| DC7134 [c] | — | — | — | — | 1.225 | 1.225 | — | — |
| DC8177 [d] | — | — | — | — | — | — | 1.225 | 1.225 |
| DMDM Hydantoin | 0.055 | 0.055 | 0.055 | 0.055 | 0.055 | 0.055 | 0.055 | 0.055 |
| CIT/MIT | 0.001 | 0.001 | 0.001 | 0.001 | 0.001 | 0.001 | 0.001 | 0.001 |
| MF particle | 0.500 | — | 0.500 | — | 0.500 | — | 0.500 | — |
| Particle of Example 1 | — | 0.500 | — | 0.500 | — | 0.500 | — | 0.500 |
| Water | to 100 | to 100 | to 100 | to 100 | to 100 | to 100 | to 100 | to 100 |

[a] DC193, 100% of active, INCI name: PEG-12 Dimethicone, ex Dow Corning.
[b] DC949, 35 wt % of active, INCI name: Amodimethicone and cetrimonium chloride and trideceth-12, ex Dow Corning.
[c] DC7134, 70 wt % of active (6.8 wt % of amodimethicone and 63.2 wt % of dimethicone), INCI name: Dimethicone (and) Amodimethicone (and) PEG-7 Propylheptyl Ether (and) Cetrimonium Chloride ex Dow Corning.
[d] DC8177, 13% of active, INCI name: amodimethicone (and) C12-14 Sec-Pareth-7 (and) C12-14 Sec-Pareth-5, ex Dow Corning.

Example 3

This example demonstrates the effect of different particles on the silicone deposition efficiency on virgin hair.

Hair switches (virgin hair having length of 5.5 cm and weight of 750 mg, or tip hair having length of 5.5 cm and weight of 350 mg) were soaked into aqueous solution of 14 wt % of SLES at 40° C. with continuous shaking for 30 minutes. Then these hair switches were rinsed by tap water thoroughly and dried at ambient environment overnight.

The hair switch was wetted with tap water and swung to remove excess water. The hair switch was washed with 0.12 g of one sample in Table 1 and then rinsed by 500 ml of tap water. The hair switches were aligned by combing and dried naturally overnight. The amount of silicone for each sample was quantitatively measured by X-ray fluorescence spectroscopy.

Table 2 shows the deposition results on virgin hair via incorporating the particles into conditioner base. The averages and standard derivations were calculated from 5 tests.

TABLE 2

| Sample | Silicone | Viscosity of silicone (cSt) | Particle | Deposition of silicone on virgin hair (ppm) |
|---|---|---|---|---|
| A | DC193 | 260 | MF | 226 ± 157 |
| B | DC193 | 260 | MF-graft-Chitosan-Arg | 216 ± 54 |
| C | DC949 | 2,000 | MF | 869 ± 215 |
| D | DC949 | 2,000 | MF-graft-Chitosan-Arg | 500 ± 60 |
| E | DC7134 | 600,000 | MF | 423 ± 46 |
| 1 | DC7134 | 600,000 | MF-graft-Chitosan-Arg | 1900 ± 193 |
| F | DC8177 | 15,000 | MF | 598 ± 78 |
| 2 | DC8177 | 15,000 | MF-graft-Chitosan-Arg | 1209 ± 172 |

As can be seen from Table 2, it was surprisingly found that the deposition of silicone of the present invention on hair was significantly enhanced by incorporating particle of the present invention into the hair conditioner.

The invention claimed is:

1. A personal care composition comprising:
   a) a particle,
      wherein the particle comprises:
         a benefit agent inside of an inner shell; and
         an outer shell,
            wherein the outer shell comprises a chitosan-amino acid salt at an outer surface of the particle; and
            wherein the ratio of the chitosan-amino acid salt to the inner shell is 1:3;
   b) a silicone component selected from the group consisting of dimethicone, aminosilicone or a mixture thereof, wherein the silicone component has a viscosity of at least 5,000 cSt at 25° C.; and
      wherein the weight ratio of the particle to the silicone component is from 1:20 to 5:1.

2. The composition according to claim 1 wherein the silicone component comprises dimethicone.

3. The composition according to claim 1 wherein the silicone component is present in an amount of 0.1 to 5% by weight of the composition.

4. The composition according to claim 1 wherein the benefit agent is a fragrance.

5. The composition according to claim 1 wherein the inner shell comprises a water insoluble non-polysaccharide polymer, a water insoluble inorganic salt or a mixture thereof.

6. The composition according to claim 5 wherein the inner shell comprises polystyrene, polyvinyl alcohol, polyacrylate, polymethacrylates, polyolefins, aminoplast polymer, polyacrylamide, acrylate-acrylamide copolymer, melamine-formaldehyde condensate, urea-formaldehyde condensate, polyurethane, polysaccaharide or a mixture thereof.

7. The composition according to claim 1 wherein the particle has an average particle diameter of 0.5 to 20 μm.

8. The composition according to claim 1 wherein the chitosan-amino acid salt is bonded to the inner shell by means of a covalent bond.

9. The composition according to claim 1 wherein the silicone component has a viscosity of from 10,000 to 10,000,000 cSt.

10. The composition according to claim 1 wherein the composition additionally comprises a cationic surfactant.

11. The composition according to claim 1 wherein the composition is a hair conditioner.

* * * * *